United States Patent [19]

Cheng et al.

[11] Patent Number: 5,834,421
[45] Date of Patent: Nov. 10, 1998

[54] METHODS AND COMPOSITIONS FOR TREATING CYSTIC FIBROSIS

[75] Inventors: Seng Hing Cheng, Wellesley; Canwen Jiang, Marlboro, both of Mass.

[73] Assignee: Genzyme Corporation, Framingham, Mass.

[21] Appl. No.: 807,398

[22] Filed: Feb. 27, 1997

[51] Int. Cl.$^6$ .......................... A01N 37/18; A61K 38/00
[52] U.S. Cl. .............................. 514/2; 514/540; 514/588; 514/619; 560/33; 564/59; 564/160; 564/161; 564/192
[58] Field of Search ................................ 514/2, 540, 588, 514/619; 560/33; 564/59, 160, 161, 192

[56] References Cited

U.S. PATENT DOCUMENTS

| | | | |
|---|---|---|---|
| 5,637,613 | 6/1997 | Renault et al. | 514/540 |
| 5,674,898 | 10/1997 | Cheng et al. | 514/517 |

OTHER PUBLICATIONS

Cheng, S.H. et al. Defective intracellular transport and processing of CFTR is the molecular basis of most cystic fibrosis. *Cell* 63:827–834 (1990).

Jensen, T.J., Loo, M.A., Pind, S., Williams, D.B., Goldberg, A.L., and Riordan, J.R. Multiple proteolytic systems including proteasome, contribute to CFTR processing. *Cell* 83:129–135 (1995).

Ward, C.L., Omura, S., & Kopito, R.R. Degradation of CFTR by the uniquitin–proteasome pathway. *Cell* 83:121–127 (1995).

Denning, G.M., Anderson, M.P., Amara, J.F., Marshall, J., Smith, A.E., and Welsh, M.J. Processing of mutant cystic fibrosis transmembrane conductance regulator is temperature–sensitive. *Nature* 358:761–764 (1992).

Brown, C.R., Hong–Brown, L.Q., Biwersi, J., Verkman, A.S., and Welch, W.J. Chemical chaperones correct the mutant phenotype of the ΔF508 cystic fibrosis transmembrane conductance regulator protein. *Cell Stress & Chaperones* 1:117–125 (1996).

Sato, S., Ward, C.L., Krouse, M.E., Wine, J.J., & Kopito, R.R. Glycerol reverses the misfolding phenotype of the most common cystic fibrosis mutation. *J. Biol. Chem.* 271:635–638 (1996).

Cheng, S.H. et al. Functional activation of the cystic fibrosis trafficking mutant κ–CFTR by overexpression. *Am. J. Physiol.* 268:L615–L624 (1995).

Hartl, F.U. Molecular chaperones in cellular protein folding. *Nature* 381:571–580 (1996).

Yang, Y., Janich, S., Cohn, J.A., and Wilson, J.M. The common variant of cystic fibrosis transmembrane conductance regulator is recognized by hsp70 and degraded in a pre–Golgi nonlysosomal compartment. *Proc. Natl. Acad. Sci. USA* 90:9480–9484 (1993).

Pind, S., Riordan, J.R., and Williams, D.B. Participation of the endoplasmic reticulum chaperone calnexin (p88, IP90) in the biogenesis of the cystic fibrosis transmembrane conductance regulator. *J. Biol. Chem.* 269:12784–12788 (1994).

Umezawa, H. et al. Structure of antitumor antibiotic, spergualin. *J. Antibiotics* 34:1622–1624 (1981).

Nadler, S.G., Tepper, M.A., Schacter, B., and Mazzucco. Interaction of the immunosuppressant deoxyspergualin with a member of the Hsp70 family of heat shock proteins. *Science* 258:484–486 (1992).

Nadeau, K., Nadler, S.G., Saulnier, M., Tepper, M.A., and Walsh, C.T. Quanitation of the interaction of the immunosuppressant deoxyspergualin and analogs Hsc70 and Hsp90. *Biochemistry* 33:2561–2567.

Marshall, J. et al. Stoichiometry of recombinant cystic fibrosis transmembrane conductance regulator in epithelial cells and its functional reconstitution into cells in vitro. *J. Biol. Chem.* 269:2987–2995 (1994).

Jefferson, D.M. et al. Expression of normal and cystic fibrosis phenotype by continuous airway epithelial cell lines. *Am. J. Physiol.* 259:L496–L505 (1990).

Tepper, M.A., Nadler S.G., Esselstyn, J.M., and Sterbenz, K.G. Deoxyspergualin inhibits κ light chain expression in 70Z/3 pre–B cells by blocking lipoplysaccharide–induced NF–κB activation. *J. Immunol.* 155:2427–2436 (1995).

Yankaskas, J.R. et al. Papilloma virus immortalized tracheal epithelial cells retain a well–differentiated phenotype. *Am. J. Physiol.* 264:C1219–C1230 (1993).

Grubman, S.A. et al. Correction of the cystic fibrosis defect by gene complementation in human intrahepatic biliary epithelial cell lines. *Gastroenterology* 108:584–592 (1995).

Dalemans, W. et al. Altered chloride ion channel kinetics associated with ΔF508 cystic fibrosis mutation. *Nature* 354:526–528 (1991).

Howard, M., Frizzell, R.A., and Bedwell, D.M. Aminoglycoside antibiotics restore CFTR function by overcoming premature stop mutations. *Nature Genetics* 2:467–469 (1996).

Rubenstein, R.C., Brusilow, S.W., Hamosh, A., and Zeitlin, P.L. Clinical trials of 4–phenylbutyrate for correction of sweat duct abnormalities in ΔF508 homozygous cystic fibrosis patients. *Pediat. Pulmonology* 13:259 (1996).

NoBner, E., Goldberg, J.E., Naftzger, C., Lyu, S.C., Clayberger, C., and Krensky, A.M. HLA–derived peptides which inhibit T cell function bind to members of the heat–shock protein 70 family. *J. Exp. Med.* 183:339–348 (1996).

Yang, I.C.H., Cheng, T.H., Wang, F., Price, E.M., and Hwang, T.C. Modulation of CFTR chloride channels by calyculin A and genistein. *Am. J. Physiol.* 272:C142–C155 (1997).

Hamill, O.P., Marty, A., Neher, E., Sakmann, B., and Sigworth, F.J. Improved patch clamp techniques for high resolution current recordings from cells and cell–free membrane patches. *Pfluger Archiv.* 391:85–100 (1981).

(List continued on next page.)

*Primary Examiner*—Cecilia J. Tsang
*Assistant Examiner*—Bennett Celsa

[57] ABSTRACT

Methods and compositions for treating CF by mobilizing mutant forms of CFTR, which retain at least some functional activity, to the plasma membrane where they can mediate chloride ion transport are disclosed.

6 Claims, 9 Drawing Sheets

OTHER PUBLICATIONS

Egan, M.E., et al. Defection regulation of outwardly rectifying chloride channels by protein kinase A corrected by insertion of CFTR. *Nature* 358:581–584 (1992).

Anderson, M.P. et al. Demonstration that CFTR is a chloride channel by alteration of its anion selectivity. *Science* 253:202–205 (1991).

Nadler, S.G. et al. Elucidating the Mechanism of Action of the Immunosuppressant 15–Deoxyspergualin. *Therapeutic Drug Monitoring* 17:700–703 (1995).

Halloran, P.F. Molecular mechanisms of new immunosuppressants. *Clinical Transplantation* 10:118–123 (1996).

Edgington, S.M. Therapeutic Applications of Heat Shock Proteins. *Bio/Technology* 13:1442–1444 (1995); and.

Sheppard D.N. and Ostedgaar, L.S. Understanding how cystic fibrosis mutations cause a loss of Cl–channel function. *Mol. Med. Today* 2(7):290–297 (1996).

Medline AN 97365770, Brown et al., Cell Stress Chaperones (1996 Jun.) 1(2) 117–25.

Yang et al., PNAS USA vol. 90 pp. 9480–9484 Oct. 1993.

METHODS AND COMPOSITIONS FOR TREATING CYSTIC FIBROSIS

BACKGROUND OF THE INVENTION

Cystic Fibrosis (CF) is the most common fatal genetic disease in humans (Boat et al. (1989), Cystic Fibrosis, In: *THE METABOLIC BASIS OF INHERITED DISEASE*, Scriver, Beaudet, Sly and Valle, eds., McGraw Hill, New York, pp. 2649–2860). Based on both genetic and molecular analysis, a gene associated with CF was isolated as part of 21 individual cDNA clones and its protein product predicted (Kerem et al. (1989), *Science* 245:1073–1080; Riordan et al. (1989), *Science* 245:1066–1073; Rommens et al. (1989), *Science* 245:1059–1065).

The product of the CF-associated gene, the cystic fibrosis transmembrane conductance regulator (CFTR), is a protein of approximately 1480 amino acids made up of two repeated elements, each having six transmembrane segments and a nucleotide binding domain. The two repeats are separated by a large, polar, so-called R-domain containing multiple potential phosphorylation sites. Based on its predicted domain structure, CFTR is a member or a class of related proteins which includes the multi-drug resistance (MDR) or P-glycoprotein, bovine adenyl cyclase, the yeast STE6 protein as well as several bacterial amino acid transport proteins (Riordan et al., supra; Hyde et al. (1990), *Nature* 346:362–365). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan et al., supra; Frizzell et al., supra.; Welsh and Liedtke (1986), *Nature* 322:467; Li et al., supra; Hwang et al. (1989), *Science* 244:1351–1353).

Sequence analysis of the CF associated gene has revealed a variety of mutations (Cutting et al. (1990a) *Nature* 346:366–369; Cutting et al. (1990b), *Am. J. Hum. Genet.* 47:213; Dean et al. (1990) *Cell* 61:863–870; Kerem et al. (1989), *Science* 245:1073–1080; and Kerem et al. (1990) *Proc. Natl. Acad. Sci., USA* 87:8447–8451). Mutations in the gene encoding CFTR result in the synthesis of aberrant variants that are either unstable, mislocalized, or whose Cl⁻ channel activity is dysfunctional as a consequence of defective regulation or conduction (Welsh and Smith (1993) *Cell* 73:1251–1254). Over 200 different mutations have been described to date, but by far the most prevalent is a deletion of the three nucleotides that encode phenylalanine at position 508 ($Phe^{508}$) located within the first nucleotide binding domain of CFTR (Tsui, L.C. (1992) *Hum. Mutat.* 1:197–203). The $Phe^{508}$ deletion ($\Delta F508$) is associated with approximately 70% of the cases of cystic fibrosis.

Studies on the biosynthesis (Cheng et al., *Cell* 63:827–834 (1990); Gregory et al. (1990) *Nature* 347:382–386) and localization (Denning et al. (1992) *J. Cell Biol.* 118:551–559) of $\Delta F508$, as well as other CFTR mutants, indicate that many CFTR mutant proteins are not processed correctly and, as a result, are not delivered to the plasma membrane (Gregory et al., supra). These conclusions are consistent with earlier functional studies which failed to detect cAMP stimulated Cl⁻ channels in cells expressing CFTR $\Delta F508$ (Rich et al., supra; Anderson et al. (1991), *Science* 251:679–682).

It is believed that the deletion of residue 508 in $\Delta F508$-CFTR prevents the nascent protein from folding correctly, and consequently the variant is recognized by the quality control mechanism present within the endoplasmic reticulum (ER) to select out against misfolded or mutant proteins (Cheng et al. supra.; Gregory et al. supra.). The mutant $\Delta F508$-CFTR bears carbohydrate structures characteristic of glycosylation at the ER and is eventually degraded. The inability of this mutant protein to exit the ER, to pass through the Golgi where it normally would be fully glycosylated, and traffic to the plasma membrane most likely accounts for the defective Cl⁻ transport found in CF epithelia harboring this mutation (Quinton, P. M. (1990) *FASEB J.* 4:2709–2727). Studies have shown, however, that $\Delta F508$-CFTR, when presented at the plasma membrane is functional as a cAMP-responsive Cl⁻ channel (Dalemans et al. (1991) *Nature Lond.* 354:526–528; Denning et al. supra.; Pasyk and Foskett (1995) *J. Cell. Biochem.* 270:12347–50).

Thus, there is a need in the art for methods and compositions which enable relocation of mislocalized CFTR mutants which retain at least some functional activity (i.e., $\Delta F508$) to the plasma membrane of epithelial cells where they can effectively mediate chloride ion transport and restore sufficient membrane conductance. The present invention satisfies this need and provides related advantages as well.

SUMMARY OF THE INVENTION

The present invention pertains to methods for treating a subject having cystic fibrosis (CF). The methods involve the administration of an effective amount of an agent that facilitates the delivery of the mutant CFTR to the plasma membrane to the subject having CF. The agent interferes with and/or modulates the functioning of molecular chaperone proteins thereby allowing the mutant CFTR protein to escape from the ER, proceed to the plasma membrane and provide functional cAMP-responsive Cl⁻ channels.

The present invention further pertains to a method for treating a subject's lung epithelia containing a mutant CFTR protein. The method involves contacting a subject's lung epithelia with an agent which interferes with and/or modulates the functioning of molecular chaperone proteins thereby allowing the mutant CFTR protein to escape from the ER, proceed to the plasma membrane and provide functional cAMP-responsive Cl⁻ channels.

The present invention even further pertains to a method for treating a subject having CF by administering an effective amount of an agent that interferes with and/or modulates the functioning of molecular chaperone proteins thereby allowing the mutant CFTR protein to escape from the ER, proceed to the plasma membrane and provide functional cAMP-responsive Cl⁻ channels.

Other aspects of the present invention include therapeutic compositions and packaged drugs for treating subjects having CF. The therapeutic compositions include a therapeutically effective amount of the forementioned agents, and a pharmaceutically acceptable carrier. The packaged drug includes the forementioned agents and instructions for administrating the agent for treating subjects having CF.

The present invention further provides methods and compositions for treating CF by mobilizing mutant forms of CFTR, which retain at least some functional activity, to the plasma membrane where they can mediate chloride ion transport are disclosed.

Accordingly, the invention described herein relates to methods and compositions useful for delivering mutant cystic fibrosis transmembrane regulator (CFTR) proteins, which retain at least some functional activity, to the plasma membrane of epithelial cells, where they can mediate chloride ion transport.

The above discussed and many other features and advantages of the present invention will become better understood by reference to the following detailed description when taken in conjunction with the accompanying drawings.

DETAILED DESCRIPTION OF THE INVENTION

Figure 1:
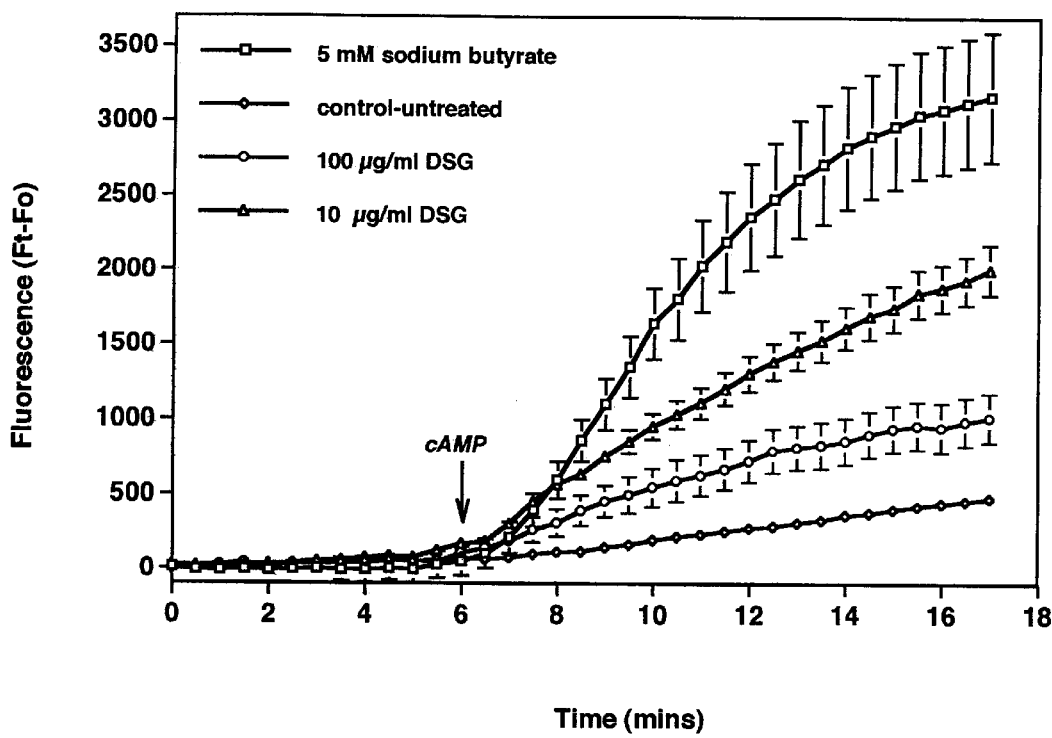
FIG. 1 shows the effects of DSG on recombinant C127-ΔF508-CFTR cells.

All patent applications, patents, and literature references cited in this specification are hereby incorporated by reference in their entirety. In case of conflict or inconsistency, the present description, including definitions, will control.

The language "pharmaceutically acceptable salt" is art-recognized terminology. Typically these salts are capable of being hydrolyzed or solvated under physiological conditions. Examples of such salts include, sodium, potassium, and hemisulfate. The term further is intended to include lower hydrocarbon groups capable of being hydrolyzed or solvated under physiological conditions, i.e. groups which esterify the carboxyl group, e.g. methyl, ethyl, and propyl.

The chaperone modulating agents of the present invention can be purchased or alternatively can by synthesized using conventional techniques.

The language "effective amount" is intended to include that amount sufficient or necessary to significantly reduce or eliminate a subject's symptoms associated with CF. The amount can be determined based on such factors as the type and severity of symptoms being treated, the weight and/or age of the subject, the previous medical history of the subject, and the selected route for administration of the agent. The determination of appropriate "effective amounts" is within the ordinary skill of the art.

The term administration is intended to include routes of administration which allow the agent (e.g., protein enhancing agent) to perform its intended function, e.g., increasing the level of at least one cellular protein. Examples of routes of administration which can be used include injection (subcutaneous, intravenous, parenterally, intraperitoneally, etc.), oral, inhalation, transdermal, and rectal. Depending on the route of administration, the agent can be coated with or in a material to protect it from the natural conditions which may detrimentally effect its ability to perform its intended function. The administration of the agent is done at dosages and for periods of time effective to significantly reduce or eliminate the symptoms associated with CF. Dosage regimes may be adjusted for purposes of improving the therapeutic response of the agent. For example, several divided doses may be administered daily or the dose may be proportionally reduced as indicated by the exigencies of the therapeutic situation.

The language "CF-associated cell" is intended to include a cell associated with CF which contains normal and/or mutant CFTR. Examples of such cells include airway epithelial cells such as nasal and lung epithelia.

The present invention further pertains to therapeutic compositions for treating a subject having CF. The composition contains a therapeutically affective amount of a chaperone modulating agent and a pharmaceutically acceptable carrier.

The language "therapeutically effective amount" is that amount sufficient or necessary to significantly reduce or eliminate a subject's symptoms associated with CF. The amount can vary depending on such factors as the severity of the symptoms being treated, the size of the subject, or the selected route for administration of the agent.

The language "pharmaceutically acceptable carrier" is intended to include substances capable of being co-administered with the agent and which allow the agent to perform its intended function, e.g. increasing the intracellular level of at least once cellular protein or inducing differentiation. Examples of such carriers include solvents, dispersion media, delay agents and the like. The use of such media and agents for pharmaceutically active substances is well known in the art. Any conventional media and agent compatible with the agent can be used with this invention. The agent of this invention can be administered alone or in a pharmaceutically accepted carrier. The agents further can be administrated as a mixture of agents which also can be in a pharmaceutically acceptable carrier. The agent further can be co-administered with other different art-recognized protein enhancing agents, differentiating agents, and/or adjuvants.

The present invention further pertains to a packaged drug for treating a subject having CF. The packaged drug includes a container holding an agent described above and instructions for administering the agent for treating a subject having CF. Examples of containers include vials, syringes, etc. The instructions would contain dosage information for administering the agent as described above.

One aspect of the instant invention provides that the molecular basis of most cystic fibrosis is the inability of the CFTR gene product to mature. That is to say, the failure of CFTR to move through the normal pathway of intracellular trafficking and modification means that the mature protein is absent from its final cellular destination in CF cells. In normal cells nascent CFTR interacts first with the endoplasmic reticulum and is then glycosylated at least one of Asn residues 894 and 900. The native molecule is then transported to the Golgi where carbohydrate processing to complex-type glycosylation occurs. Finally, at least some of the mature glycosylated molecule is thereafter transported to the plasma membrane.

It is now reasonably well established that the endoplasmic reticulum possesses a mechanism that prevents transport of mutant, misfolded or incorrectly complexed versions of proteins otherwise destined for further processing (Lodish, 1988; Rose and Doms, 1988; Pelham, 1989; Hurtley and Helenius, 1989; Klausner and Sitia, 1990). If this quality control mechanism operates on CFTR, it would prevent transport to the Golgi and consequently, further modification of several of the mutants reported here. As a result, the unmodified mutant versions of the protein either would not exit the endoplasmic reticulum and would subsequently be degraded therein, or alternatively, they would be transported to the lysosomes for degradation.

It is not clear how the quality control mechanism recognizes the difference between wild-type and those mutant versions of CFTR which were not further processed. One obvious mechanism would be that an alteration in structure of the molecule is detected. Indeed, gross changes in structure of the first nucleotide binding domain (and perhaps in consequence of the whole molecule) might be expected following deletion of phenylalanine 508. However, it is not clear how this change in structure would be detected by a mechanism located, for example, in the lumen of the endoplasmic reticulum, since the domain bearing the mutation, would lie on the cytosolic side of the membrane. Perhaps the structural change is transmitted across the membrane or perhaps the sensing mechanism does not recognize CFTR directly, but rather detects a protein with which it is complexed. In this case, all mutations within CFTR that prevent complex formation also prevent intracellular transport. Yet another mechanism would be that nascent CFTR has basal activity in the endoplasmic reticulum and that mutations that disrupt this activity are sensed by the quality control mechanism. Perhaps some activity of CFTR is necessary for its maturation and by this means, enzymatically inactive proteins are marked for degradation. Irrespective of the mechanism of discrimination, the time course of synthesis of both wild-type and mutant CFTR is notable in two respects. Firstly, the half life of band B is similar for both wild-type and mutant versions and secondly, most of the wild-type band B appears to be degraded. One interpretation of these results is that synthesis of CFTR involves two steps, retention in the endoplasmic reticulum during which time folding of the protein occurs followed by either export to the Golgi or degradation.

The most common cause of cystic fibrosis is deletion of the phenylalanine residue at position 508 (ΔF508) of the cystic fibrosis transmembrane conductance regulator (CFTR). Studies have shown that this mutation results in the synthesis of a variant CFTR (ΔF508-CFTR) that is retained in the endoplasmic reticulum (ER) where it is rapidly degraded (Cheng et al. (1990), *Cell* 63:827–834). As ΔF508-CFTR retains significant cAMP-stimulated chloride channel activity, strategies that result in the relocation or escape of the mutant protein from the ER to the plasma membrane may be therapeutically beneficial.

To date, several approaches have been described that can facilitate the presentation of ΔF508-CFTR at the cell surface. These include (i) lowering the temperature (Denning et al. (1992), *Nature* 358:761–764) (ii) overexpression of the mutant protein using butyrate (Cheng et al. (1995), *Am. J. Physiol.* 268:L615–L624) and (iii) treatment with glycerol (Sato et al. (1996), *J. Biol. Chem.* 271:635–638).

The mechanisms that result in the retention of the mutant CFTR in the ER have also been studied. One explanation for the retention of CFTR mutations in the ER may be the presence of molecular chaperones in both the ER and the cytosol that prevent newly synthesized proteins from folding inappropriately during processing. Once a protein is correctly folded, it then moves to the Golgi. The immature or band B form of both wild-type CFTR and mutant ΔF508-CFTR have been shown to interact with the chaperones calnexin and hsp70 (Pind et al. (1994), *J. Biol. Chem.* 269:12784–12788; Yang et al. (1993), *Proc. Natl. Acad. Sci., USA* 90:9480–9484). However, only wild-type CFTR is able to dissociate from either calnexin and hsp70 and exit the ER. Both calnexin and hsp70 reportedly retain band B ΔF508-CFTR in the ER and this, it is proposed, contributes to the mislocalization of the mutant CFTR. While interaction of most wild-type CFTR with hsp70 is transient, ΔF508 CFTR forms a stable complex with hsp70 and is degraded in a pre-Golgi nonlysosomal compartment.

Given that ΔF508 CFTR has been shown to be functionally competent when it is able to reach the plasma membrane, methods and compositions which promote trafficking of this mutant to the plasma membrane provide the basis of novel approaches to CF therapy. Accordingly, the present invention provides methods and compositions capable of disrupting the CFTR-molecular chaperone complex. For example, drugs active in altering the activity and distribution of hsp70 proteins could advantageously be used to redistribute to the plasma membrane mutant CFTR which retains at least some functional activity. Similarly, agents effective in stimulating sufficient CFTR activity to result in export of otherwise mutant CFTR to the Golgi for additional glycosylation could result in improved CFTR function in homozygous CF individuals. Alternatively, therapeutic treatment via a suitable, therapeutically effective blocking agents could be used to deactivate chaperone proteins, for example, agents that are substrates and compete for binding to hsp70.

Examples of agents that bind to hsp70, include, but are not limited to deoxyspergualin (DSG), a spermidinyl, α-hydroxyglycyl, 7-guanidinoheptanoyl peptidomimetic, and analogs thereof, for example, methoxy- and glycylDSG have been shown to bind hsps with similar affinities (Nadler et al. (1992), *Science* 258:484–486). Pure human hsp90 and hsp70 have equivalent afinities for DSG. Hsp90 is particularly abundant cytosolic protein and its concentration may approach 2–10 $\mu$M, while hsp70 can reach 5 $\mu$M. Given kds of 4–5 $\mu$M, the DSG-hsp complexes would be highly populated and DSG could compete effectively for other protein and peptide binding to hsp70 and hsp90 and thereby affect protein trafficking.

DSG, a potent immunosuppressive agent, is a synthetic derivative of a natural product originally isolated from *Bacillus laterosporus*. It has the unique ability to suppress both humoral and cell-mediated immune responses by down-regulating presentation of MHC class I or II antigen, modulating IL-1 production, and inhibiting IL-2 receptor expression. Perhaps most importantly it also has the effect of preventing monocytes from functioning as antigen-presenting cells.

It has been suggested that DSG works by blocking hsp70's ability to transport proteins, specifically NF-κβ into the nucleus (Tepper et al., (1995) *J. Immunol.* 155:2427–2436). The working hypothesis is that DSG binds to hsc70, the constitutively expressed form of the hsp 70 family, that normally serves to fold and chaperone proteins across membranes. It appears that DSG is binding at a site normally occupied by the hsp helper protein dna J, interfering with ATPase activity in a still undetermined way (Nadler et al. (1995) *Therapeutic Drug Monitoring* 17:700–703).

Accordingly, the present invention provides novel methods and compositions for treating cystic fibrosis-associated (CF-associated) cells with agents that interfere with and/or modulate the functioning of molecular chaperone proteins thereby allowing the mutant CFTR protein to escape from the ER, proceed to the plasma membrane and provide functional cAMP-responsive Cl⁻ channels.

The following examples are intended to illustrate the invention without limiting the scope thereof.

EXAMPLE 1

The Effect of DSG on Recombinant C127 Cells Expressing ΔF508 Cystic Fibrosis Transmembrane Regulator Protein Nadler et al. (1992), *Science* 258:484–486 has reported that the immunosuppressant deoxyspergualin (DSG) interacts with hsc70, a member of the hsp70 family of heat shock proteins. The $K_d$ value for DSG binding to hsc70 is 4 μM, a concentration that is within the range of a pharmacologically active dose (Nadeau et al. (1994), *Biochemistry* 33:2561–2567). Since the intracellular concentration of hsc70 is approximately 5 μM, it is possible that DSG binding to hsp70 may compete effectively for peptide or protein binding to hsp 70.

Derivation of ΔF508-C127 Cells

A bovine-papilloma virus based eukaryotic expression vector (pBPV-CFTR-ΔF508) containing the gene for ΔF508 CFTR and neomycin resistance were transfected into C127 cells. The C127 cells are murine mammary cells which were obtained from ATCC (#CRL 1616). The expression of the mutant ΔF508 protein and neomycin was driven using a metallothionein promoter. Following transfection, clonal cells resistant to G418 were isolated and cells expressing the mutant ΔF508 protein were subsequently identified using antibodies specific for CFTR (mAb-13-1). The cells expressing the mutant ΔF508 CFTR protein were maintained in Dulbecco's modified eagle media (DMEM) supplemented with glutamine and fetal calf serum.

Treatment of the ΔF508-C127 Cells with DSG and Analysis of Cells for Chloride Channel Activity To test whether treatment with DSG may interfere with the ability of hsp70 to retain ΔF508-CFTR in the ER, recombinant C127 cells expressing ΔF508 CFTR were seeded onto glass coverslips and were exposed to DSG (10 to 100 μg/ml) (Bristol Myers Squibb, Seattle, Wash.) for 48 to 72 h.

Following treatment with DSG, the cells were assayed for the presence of functional CFTR chloride channel activity at the cell surface using the halide sensitive fluorophore 6-methoxy-N-[3-sulfopropyl]quinolinium (SPQ) assay (Cheng et al. (1991) *Cell* 66:1027–1036).

Cells were loaded with SPQ by either including 10 mM SPQ in the growth media for nine to twelve hours or after hypotonic shock (with 50% vol/vol water) for 4 min at room temperature. SPQ fluorescence was initially quenched by incubating the cells in a sodium iodide buffer solution (135 mM NaI; 2.4 mM $K_2HPO_4$; 0.6 mM $KH_2PO_4$; 1.0 mM $MgSO_4$; 1.0 mM $CaSO_4$; 10.0 mM HEPES pH 7.4). After measuring the fluorescence for two minutes using a Nikon inverted microscope, a Universal Imaging System and a Hamatsu camera, the sodium iodide buffer solution was replaced by a sodium nitrate buffer solution (same as the NaI solution except $NaNO_3$ was substituted for NaI). The fluorescence was measured for an additional 17.5 minutes. SPQ fluorescence is quenched by iodide but not by nitrate. The intracellular cAMP levels were increased by adding forskolin and 3-isobutyl-1-methyl-xanthene (IBMX) five minutes after the anion substitution. In this assay (hereinafter the SPQ assay) an increase in halide permeability results in SPQ fluorescence.

In this assay, a rapid change in fluorescence upon stimulation with cAMP agonists (i.e., forskolin) is indicative of the presence of active CFTR at the plasma membrane. FIG. 1 shows that DSG-treated C127-ΔF508-CFTR cells gave a rapid change in fluorescence following stimulation with forskolin indicating that incubation with DSG effected the presence of functional CFTR activity at the cell surface. These cells, therefore, contained functional cAMP-dependent chloride channels. This activity was absent from ΔF508-C127 cells which had not been pretreated with DSG, but had been mock treated with phosphate buffered saline.

EXAMPLE 2

Figure 2:
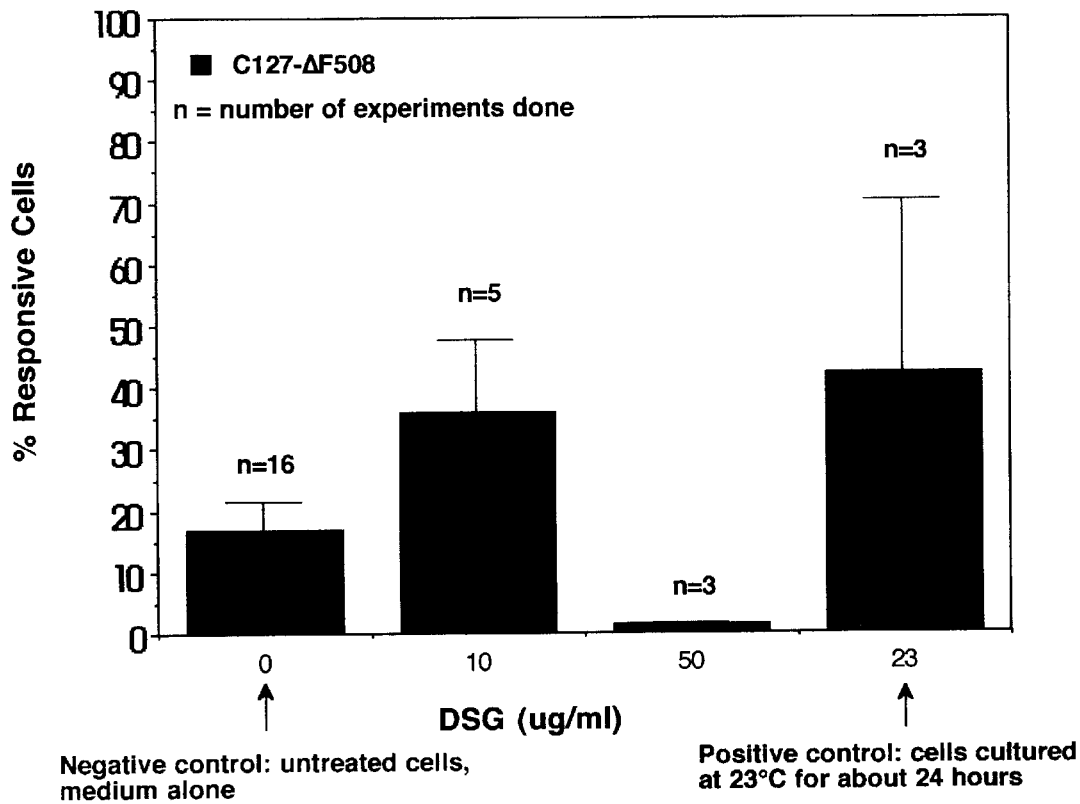
FIG. 2 shows the effects of varying concentrations of DSG on recombinant C127-ΔF508-CFTR cells.
Figure 3:
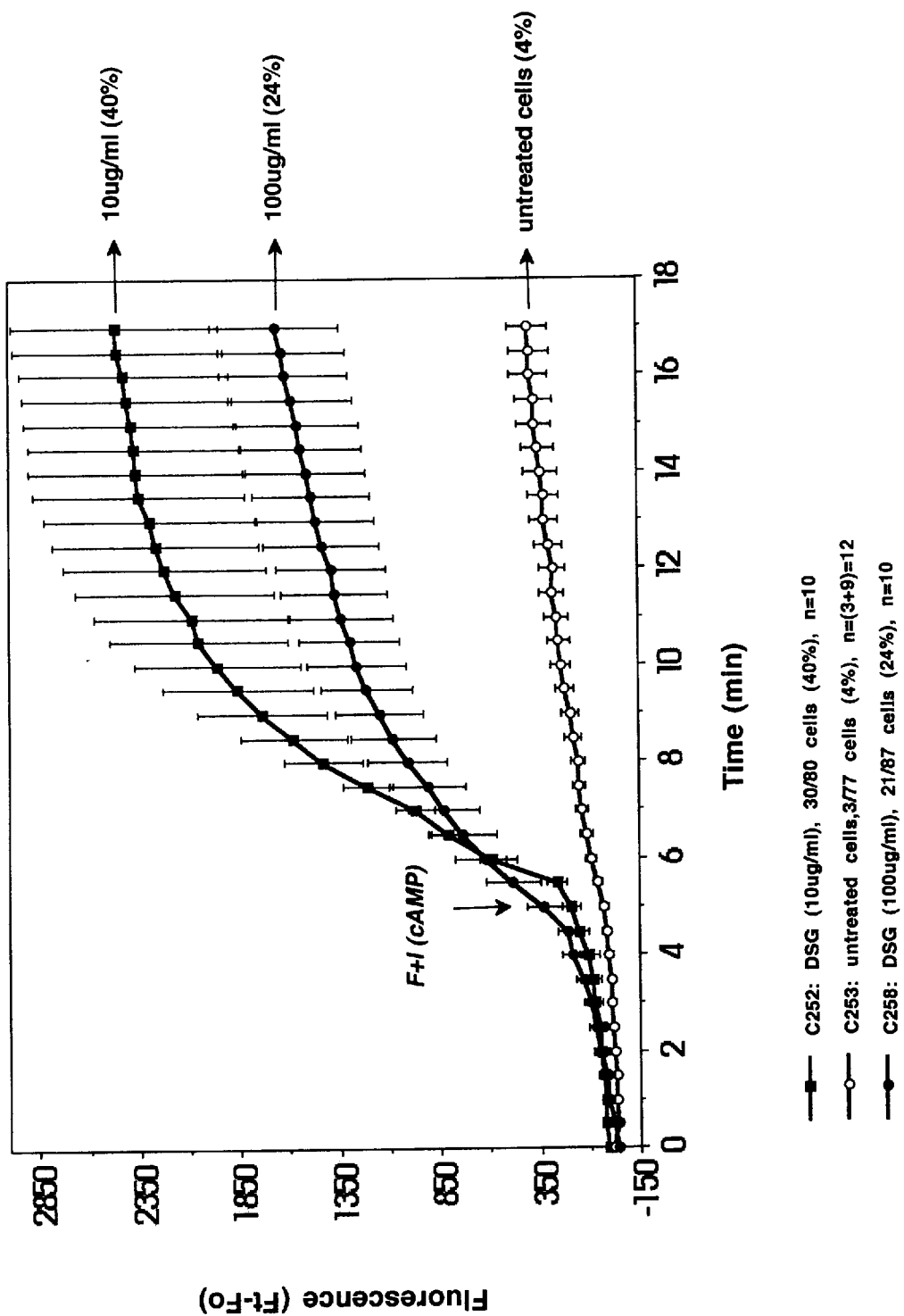
FIG. 3 summarizes the overall effects concentration of DSG on recombinant C127-ΔF508-CFTR cells at normal and reduced temperature.

The Effect of DSG Concentration on Recombinant C127 Cells Expressing ΔF508 Cystic Fibrosis Transmembrane Regulator Protein Results similar to those in Example 1 were obtained in a second experiment (FIG. 2) using different concentrations of DSG (10 μg/ml; 20 μg/ml; 50 μg/ml). More optimal responses were observed in cells that were treated with lower concentrations of DSG compared to higher concentrations of DSG. However, this difference could be attributed to cytotoxicity associated with higher concentrations of DSG. The results of the study, which are presented in FIG. 3, also indicate that percentage of mature CFTR produced from CFTRΔF508 in the presence of DSG increases upon exposure to reduced temperatures.

Under the conditions tested, the change in SPQ fluorescence observed in DSG-treated cells was less than that obtained with sodium butyrate, an agent described previously as capable of effecting the presence of ΔF508-CFTR at the plasma membrane of these cells (Cheng et al. (1995), *Am. J. Physiol.* 268:L615–L624). It is possible that with optimization of the dose of DSG, and addition of the polyamine oxidase inhibitor aminoguanidine hemisulfate to prevent the breakdown of DSG (Tepper et al. (1995), *J. Immunol.* 155:2427–2436), greater responses may be realized. Furthermore, because the mechanism of action of butyrate and DSG are likely to be different, use of both agents together may be synergistic and result in even greater levels of ΔF508-CFTR at the plasma membrane.

EXAMPLE 3

The Effect of DSG on Human Airway Epithelial Cells (JME/CF15) Expressing ΔF508 Cystic Fibrosis Transmembrane Regulator Protein Cell Culture Immortalized CF nasal airway epithelial cells (JME/CF15) generated from a ΔF508 (−/−) patient, were maintained by coculturing with lethally irradiated NIH-3T3 cells in Dulbecco's modified eagles medium/F-12 (3:1) supplemented with adenine, insulin, transferrin, triiodothyronine, hydrocortisone, cholera toxin, epidermal growth factor and 5% fetal bovine serum. Before use cells were grown to confluence to eliminate all cocultured NIH3T3 cells.

Treatment of the JME/CF15 Cells with DSG and Analysis of Cells for Chloride Channel Activity To test whether treatment with DSG may interfere with the ability of hsp70 to retain ΔF508-CFTR in the ER, JME/CF15 cells expressing ΔF508 CFTR were seeded onto glass coverslips and were exposed to DSG (10 μg/ml; 50 μg/ml; 100 μg/ml) (Bristol Myers Squibb, Seattle, Wash.) for 48 to 72 h.

Following treatment with DSG, the cells were assayed for the presence of functional CFTR chloride channel activity at the cell surface using the halide sensitive fluorophore 6-methoxy-N-[3-sulfopropyl]quinolinium (SPQ) assay (Cheng et al. (1991) *Cell* 66:1027–1036). See, also Example I above.

Figure 4:
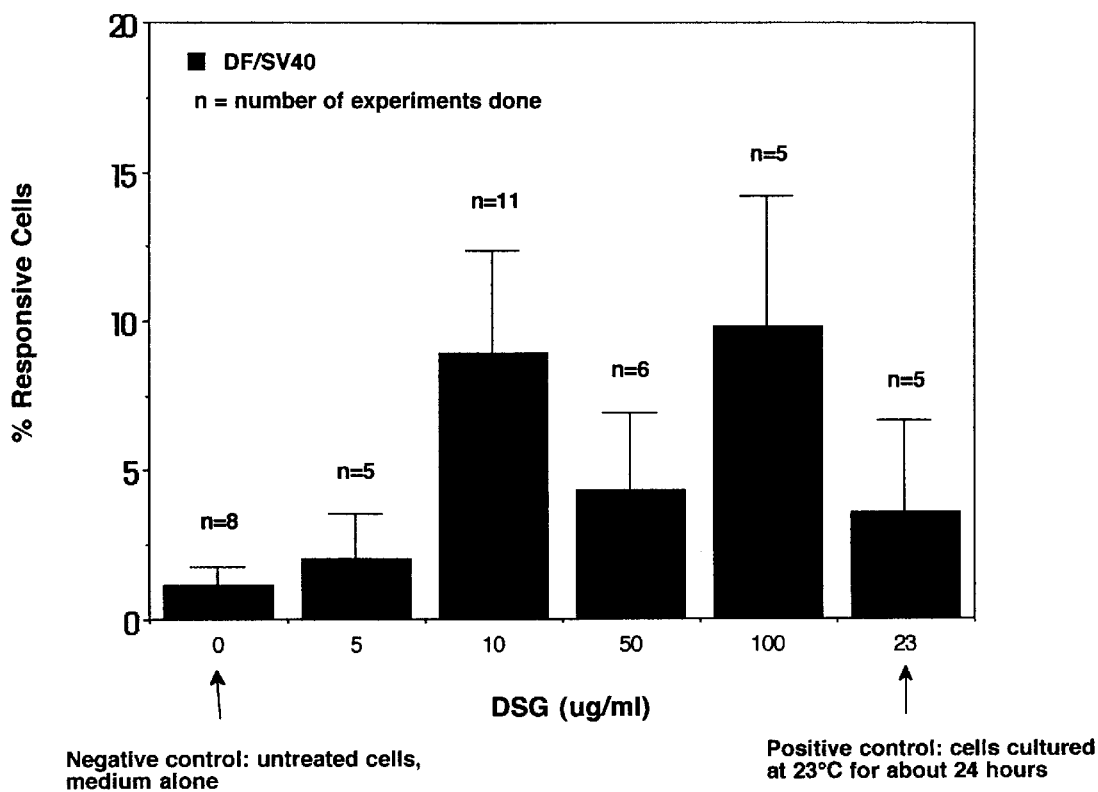
FIG. 4 shows the effects of DSG on human JME/CF15 cells.
Figure 5:
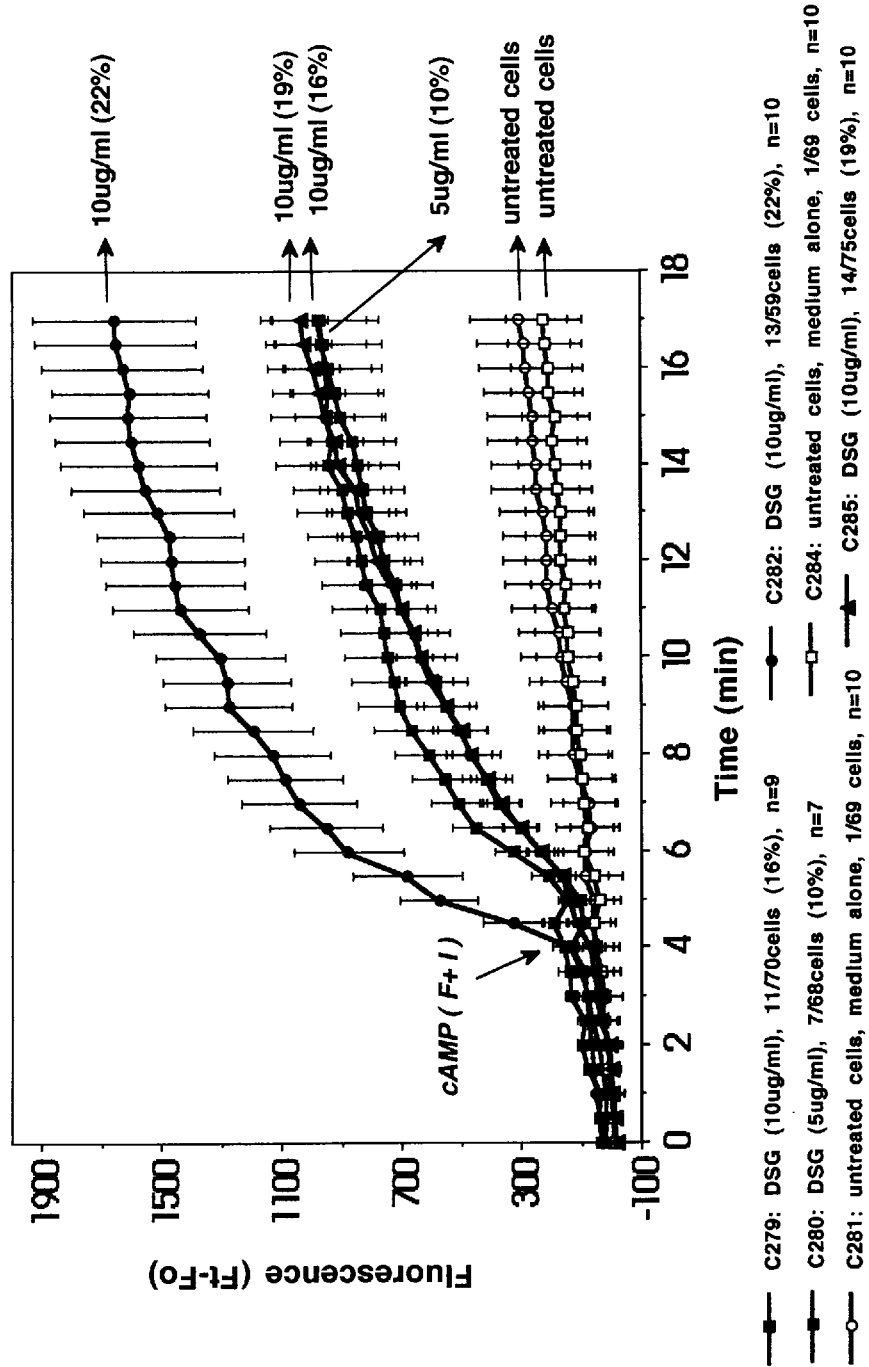
FIG. 5 shows the overall effects of varying concentrations of DSG on human JME/CF15 cells at normal and reduced temperature.

FIG. 4 shows that DSG at doses of 10, 50, and 100 μg/ml increased cAMP-mediated chloride channel activity in immortalized airway epithelial (JME/CF15) cells generated from a ΔF508 (−/−) patient measured by SPQ. The results of the study, which are presented in FIG. 5, indicate that percentage of mature CFTR produced from CFTRΔF508 in the presence of DSG increases upon exposure to reduced temperatures.

Figure 6:
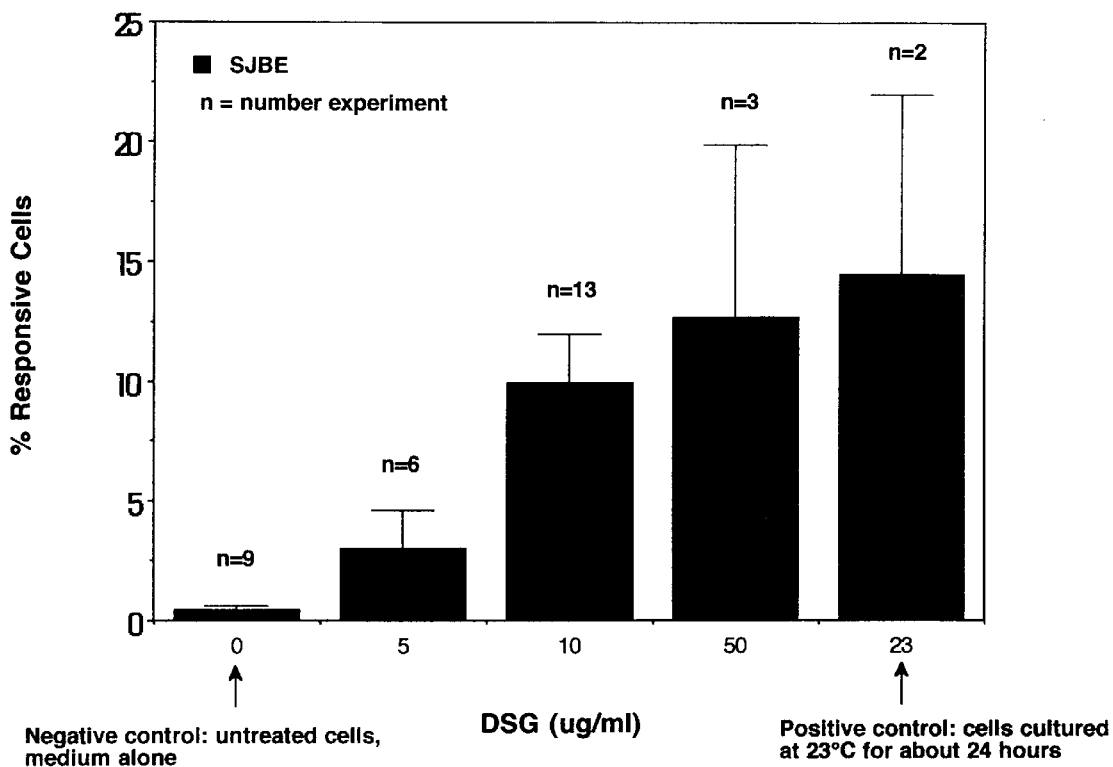
FIG. 6 shows the effects of DSG on human SJBE cells.
Figure 7:
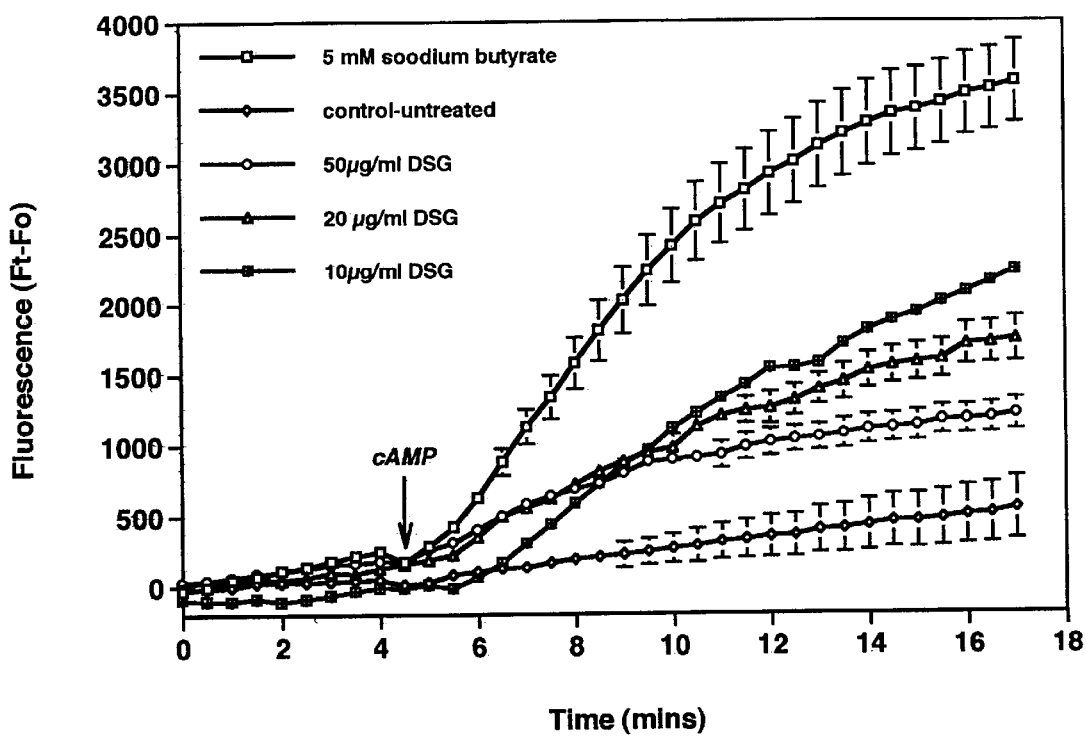
FIG. 7 shows the overall effects of varying concentrations of DSG on human SJBE cells at normal and reduced temperature.
Figure 8:
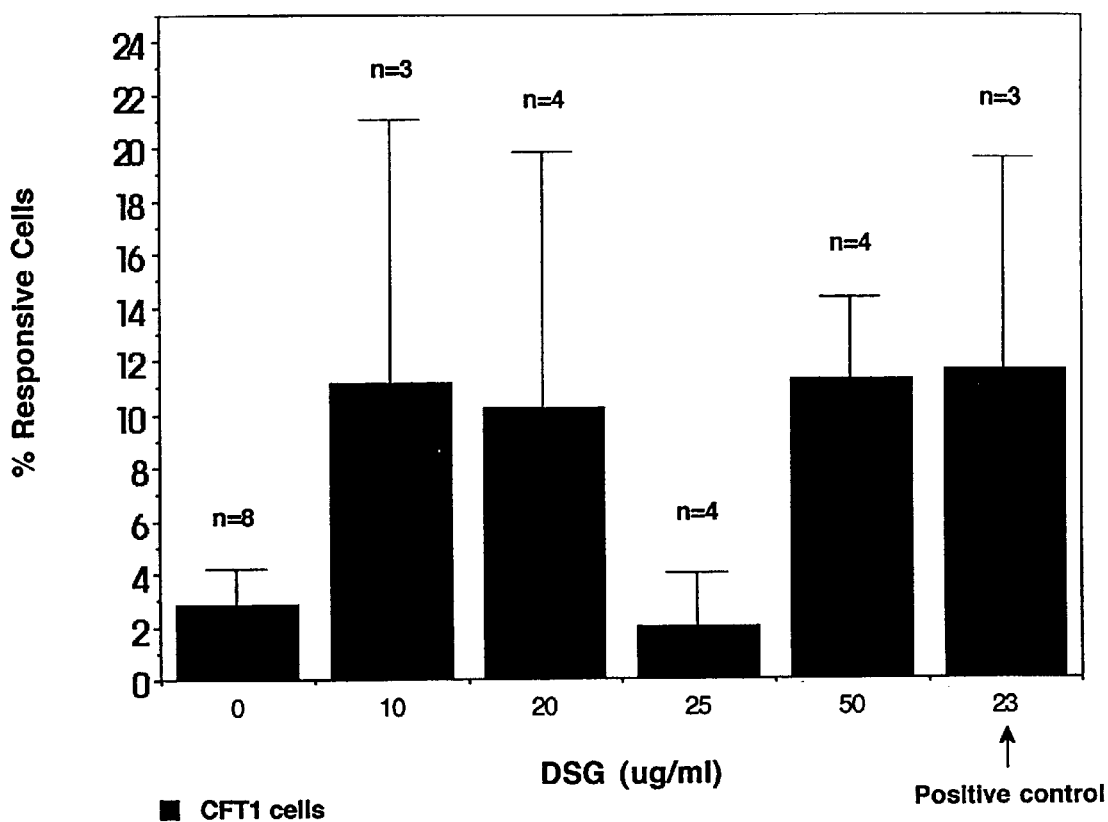
FIG. 8 shows the overall effects of varying concentrations of DSG on a bovine papilloma virus immortalized human airway epithelial cell line containing the ΔF508 variant.
Figure 9:
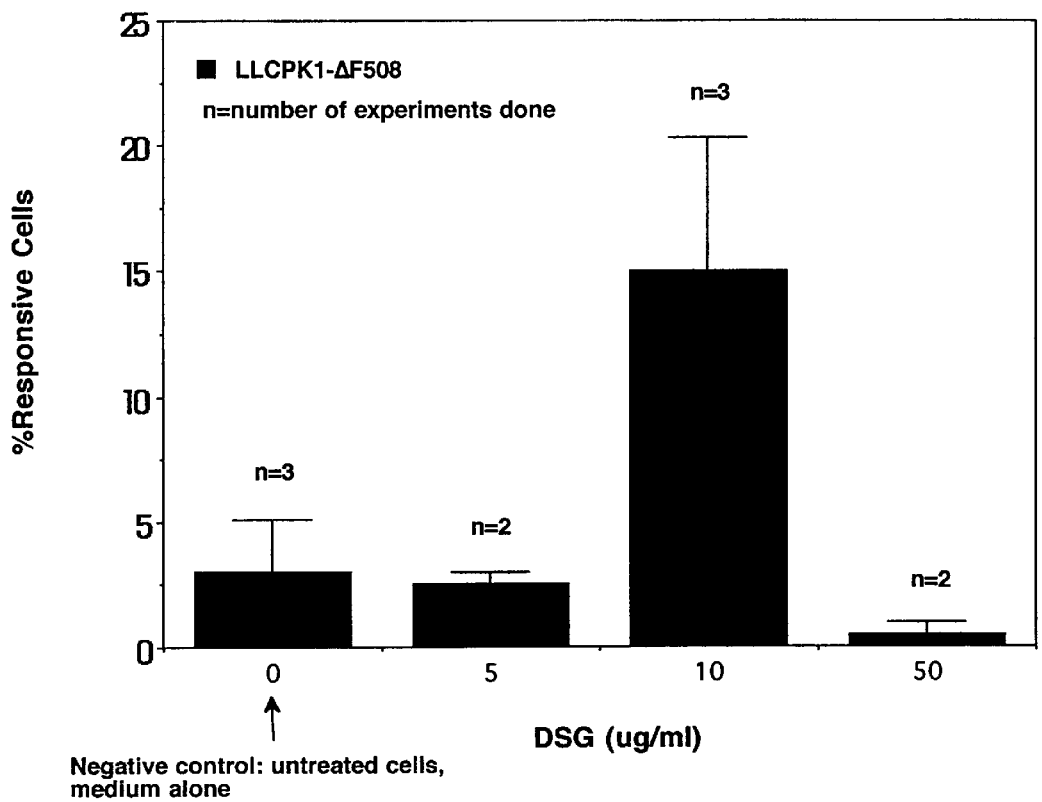
FIG. 9 shows the overall effects of varying concentrations of DSG on a pig kidney epithelial cell line containing the ΔF508 variant.

Similar results were obtained in an SV40 immortalized human intrahepatic biliary duct epithelial (SJBE) cell line containing the ΔF508 variant (FIGS. 6 and 7). However, in cell lines expressing recombinant ΔF508 under the control of a CMV promoter, namely C127 cells and LLCPK cells, the effects of DSG on cAMP-mediated chloride channel activity measured by SPQ was marginal (FIGS. 8 and 9).

These results suggest that DSG may rescue ΔF508 CFTR by affecting its trafficking in immortalized human CF epithelial cells. The mechanism, possibly through an interaction with Hsp 70, is different from that of sodium butyrate which has been shown to cause overexpression of ΔF508 in recombinant cells.

EXAMPLE 4

The Effect of DSG on Primary Airway Epithelial Cells Expressing ΔF508 Cystic Fibrosis Transmembrane Regulator Protein To test whether treatment with DSG may interfere with the ability of hsp70 to retain ΔF508-CFTR in the ER, primary tracheobronchial epithelial cells from transgenic ΔF508 (−/−) mice are seeded onto glass coverslips and exposed to varying concentrations of DSG (10 μg/ml to 100 μg/ml) (Bristol Myers Squibb, Seattle, Wash.) for a period of 3–5 days.

Following treatment with DSG, the cells are assayed for the presence of functional CFTR chloride channel activity at the cell surface using the halide sensitive fluorophore 6-methoxy-N-[3-sulfopropyl]quinolinium (SPQ) assay (Cheng et al. (1991) *Cell* 66:1027–1036). See, also Example I above.

Although the invention has been described with reference to the disclosed embodiments, those of skill in the art will understand that, using no more than routine experimentation, various modifications can be made without departing from the spirit of the invention. Such equivalents are intended to be encompassed within the scope of the following claims.

What is claimed is:

1. A method for generating chloride channels in a cystic fibrosis (CF)-associated cell, the method comprising:

contacting said cell with an amount of deoxyspergualin and/or analog thereof effective to mobilize mutant cystic fibrosis transmembrane conductance regulator (CFTR) protein in said cell such that said mutant CFTR protein is transported to the plasma membrane of said cell and generates chloride channels therein.

2. The method of claim 1 wherein the CF-associated cell is an epithelial cell.

3. The method of claim 2 wherein the epithelial cell is an airway epithelial cell.

4. A method for treating defective chloride ion transport in a subject having cystic fibrosis, the method comprising:

administering an amount of deoxyspergualin and/or analog thereof effective to allow transport of mutant cystic fibrosis transmembrane conductance regulator (CFTR) protein to the plasma membrane of a cystic fibrosis (CF)-associated cell of said subject wherein said mutant CFTR mediates chloride ion transport in the CF-associated cell of said subject.

5. The method of claim 4 wherein the CF-associated cell is an epithelial cell.

6. The method of claim 5 wherein the epithelial cell is an airway epithelial cell.

* * * * *